United States Patent [19]

Larkins, Jr.

[11] 4,337,351

[45] Jun. 29, 1982

[54] PREPARATION OF ETHYLIDENE DIACETATE

[75] Inventor: Thomas H. Larkins, Jr., Kingsport, Tenn.

[73] Assignee: Eastman Kodak Company, Rochester, N.Y.

[21] Appl. No.: 229,816

[22] Filed: Jan. 30, 1981

[51] Int. Cl.$^3$ .................... C07C 67/00; C07C 69/16
[52] U.S. Cl. .................. 560/263; 560/232; 560/265; 562/607
[58] Field of Search .......................... 560/263

[56] References Cited

U.S. PATENT DOCUMENTS 3,579,566  5/1971  Fenton ........................... 560/263
4,221,918  9/1980  Suzuki ........................... 560/263

Primary Examiner—Vivian Garner
Attorney, Agent, or Firm—J. Frederick Thomsen; Daniel B. Reece, III

[57] ABSTRACT

Process for the preparation of ethylidene diacetate by hydrogenating acetic anhydride in the presence of a ruthenium on alumina catalyst and methyl iodide.

3 Claims, No Drawings

PREPARATION OF ETHYLIDENE DIACETATE

This invention relates to a novel process for the preparation of ethylidene diacetate by hydrogenating acetic anhydride.

An economically advantageous process for the preparation of acetic anhydride by the carbonylation of methyl acetate has been reported in the patent literature. See, for example, Belgian Pat. No. 819,455, British Published Patent Application No. 2,013,184, Japanese Published Patent Applications Nos. 75-47921 and 75-47922 and U.S. Pat. Nos. 3,927,078 and 4,046,807. Not only is acetic anhydride itself an important chemical, for example as an acetylating agent in the manufacture of cellulose acetate and other esters, but it can be converted to ethylidene diacetate. The ethylidene diacetate can be converted to vinyl acetate which, at the present time, is derived primarily from petroleum.

Very little prior art exists concerning the hydrogenation of acetic anhydride. The hydrogenation of acetic anhydride to ethylidene diacetate and acetic acid with a catalyst consisting of a Group VIII noble metal and a biphyllic ligand selected from the group consisting of trihydrocarbyl phosphines, arsines, and stibines is disclosed in U.S. Pat. No. 3,579,566. With these catalysts the reaction rate was slow. Depending upon the reaction conditions and catalyst used, ethyl acetate and acetic acid were produced, along with the desired ethylidene diacetate product. The co-production of acetic anhydride and ethylidene diacetate by the carbonylation of methyl acetate in the presence of hydrogen, a Group VIII noble metal catalyst and methyl iodide is disclosed in Belgian Pat. No. 839,321. The preparation of ethylidene diacetate from acetic anhydride using a supported palladium catalyst in the presence of a strong acid, i.e., HCl, HF, or methane sulfonic acid, is disclosed in Belgian Pat. No. 879,178. When HCl was the acid used, large amounts of 1-chloroethylacetate were produced along with the desired ethylidene diacetate and acetic acid products. The hydrogenation of acetic anhydride to ethyl acetate with $Ru(X_2)(PR_3)_3$ catalyst where X is a halogen or lower alkyl and $PR_3$ is an alkyl or aryl phosphine is described in U.S. Pat. No. 3,957,827. Ber., 63B, 796 (1930) discloses the hydrogenation of acetic anhydride to ethyl acetate with a palladium black catalyst. Addition of HCl promoted the hydrogenation reaction.

The process of this invention comprises hydrogenating at elevated pressure and temperature acetic anhydride in the presence of a catalytic amount of a ruthenium on alumina catalyst and methyl iodide. The ruthenium on alumina catalyst has been found to possess significantly greater catalytic activity when compared to other supported ruthenium catalysts such as ruthenium on carbon. I have also found that the presence of methyl iodide, even in low concentrations, dramatically increases the rate of conversion of acetic anhydride to ethylidene diacetate.

The process can be carried out either by batch or continuous operation in which the supported ruthenium catalyst is present as a slurry in the reaction medium. Continuous operation is advantageously carried out using a columnar hydrogenation reactor containing one or more fixed beds of the catalyst. Acetic anhydride is fed to the column wherein it is hydrogenated at elevated temperature and pressure. Co-product acetic acid and any acetic anhydride present in the reactor effluent are separated from the ethylidene diacetate and the anhydride may be recycled to the reactor. The acetic acid produced may be esterified with methanol and the resulting methyl acetate used to produce acetic anhydride.

The catalytically-effective amount of the ruthenium on alumina catalyst that will give satisfactory results depends on a great number of variables. For example, the optimum amount of catalyst will depend on reaction conditions such as temperature, pressure and flow rates, the amount of methyl iodide present and the mode of operation of the process. The amount of ruthenium present on the alumina support and the technique by which the ruthenium is deposited on the support also would be expected to affect catalyst activity and thus the amount of the supported catalyst required to give a desired yield and/or production rate. It has been found that for a 0.5% ruthenium on alumina in a batch slurry operation, catalyst concentrations of 0.1 to 5.0, preferably 0.5 to 1.5, weight percent based on the acetic anhydride fed gives moderate to excellent results depending on other variables such as those mentioned above.

The hydrogenation-effective temperature and pressure which can be used in the process also will vary considerably since not only are the interdependent but each, especially temperature, is dependent on the amount of methyl iodide employed. Suitable temperature and pressure ranges are about 140° to 225° C. and about 300 to 2500 psig total reaction pressure. The preferred ranges are about 160°–180° C. and 500–1000 psig. As pointed out above, the inclusion of even a small amount of methyl iodide with the ruthenium on alumina catalyst in the reaction mixture significantly increases reaction rate. The lower limit on the amount of methyl iodide generally will be about 1 weight percent based on the acetic anhydride providing that other conditions are in the upper part of the ranges specified. As much as 25 weight percent may be used but ordinarily there will be no advantage in using that much. Under most conditions about 5–10 weight percent methyl iodide will give good results.

The selection of the particular set of operating conditions usually will involve a balancing of production rate versus production yield. In general, higher temperatures will give higher space time yields but lower ethylidene diacetate yields based on the acetic anhydride fed. Also, when both the temperature and methyl iodide concentration are high, undesired side reactions occur resulting in decreased yields. Similarly, the use of both high temperature and pressure cause a significant decrease in the yield of ethylidene diacetate.

The process of the invention is further illustrated by the following examples.

EXAMPLES 1-22

Acetic anhydride (100 g.) was hydrogenated for 30 minutes in the presence of 1.5 g. of a supported ruthenium catalyst using different temperatures and total autoclave pressures and varying amounts of methyl iodide. In Examples 1–14 the catalyst used was 0.5% ruthenium on alumina powder (Englehard Lot E-C-3487) and in Examples 15–22 5.0% ruthenium on carbon powder (Englehard Lot E-24195) was used. The acetic anhydride, ruthenium catalyst and methyl iodide were loaded into a 300 ml. Hastalloy B autoclave designed to operate in a rocking mode. The autoclave was purged with 100 psig hydrogen gas pressure at room temperature and then the gas was vented. The autoclave internal pressure was increased to 10 psig by adding hydrogen gas at room temperature. The autoclave was sealed and heated and rocked until reaction temperature was reached, at which time additional hydrogen gas was added to increase the autoclave internal pressure to the predetermined value. The time at which the autoclave internal pressure reached the predetermined value was taken as the start of the 30-minute reaction time. Reactor pressure was maintained at the preset value during the experiment by adding hydrogen gas at the same rate at which it was consumed by the reactants. When the predetermined reaction time was completed, the autoclave was cooled by a stream of cold air. After the gas was vented from the autoclave the reaction product was analyzed by gas chromatographic methods.

Table I shows the temperature (°C.) and pressure (psig) used, the amount of methyl iodide (CH$_3$I, g.) charged, the amounts (in moles) of acetic acid (HOAc) and ethylidene diacetate (EDA) produced, the amount of acetic anhydride (Ac$_2$O, in moles) recovered the production yield (PY, % of theory) and the space-time yield (STY, in grams/liter-hour) for ethylidene diacetate.

TABLE I

| Ex. | Temp. | Pressure | MeI | HOAc | Ac$_2$O | EDA | EDA PY | EDA STY |
|---|---|---|---|---|---|---|---|---|
| 1 | 200 | 500 | — | 0.077 | 0.959 | 0.016 | 100 | 47 |
| 2 | 200 | 500 | 1.0 | 0.242 | 0.796 | 0.085 | 92.4 | 248 |
| 3 | 200 | 500 | 5.0 | 0.508 | 0.396 | 0.251 | 86.0 | 733 |
| 4 | 200 | 500 | 9.0 | 0.532 | 0.237 | 0.309 | 83.2 | 902 |
| 5 | 200 | 500 | 15.0 | 0.561 | 0.253 | 0.296 | 81.4 | 864 |
| 6 | 170 | 500 | 15.0 | 0.336 | 0.563 | 0.193 | 92.6 | 564 |
| 7 | 200 | 500 | 5.0 | 0.677 | 0.162 | 0.33 | 80.7 | 964 |
| 8 | 170 | 1500 | 5.0 | 0.357 | 0.509 | 0.218 | 92.6 | 637 |
| 9 | 200 | 500 | 15.0 | 0.676 | 0.074 | 0.332 | 73.3 | 969 |
| 10 | 170 | 1500 | 15.0 | 0.588 | 0.233 | 0.322 | 87.6 | 955 |
| 11 | 200 | 1500 | 5.0 | 0.787 | 0.024 | 0.298 | 62.3 | 870 |
| 12 | 200 | 1500 | 15.0 | 0.988 | 0.029 | 0.217 | 45.7 | 633 |
| 13 | 170 | 500 | 5.0 | 0.230 | 0.637 | 0.141 | 82.2 | 412 |
| 14 | 185 | 1000 | 10.0 | 0.489 | 0.229 | 0.315 | 83.9 | 920 |
| 15 | 185 | 1000 | 10.0 | 0.083 | 0.892 | 0.041 | 93.2 | 120 |
| 16 | 170 | 500 | 15.0 | 0.081 | 1.00 | 0.021 | 100 | 61 |
| 17 | 200 | 500 | 5.0 | 0.236 | 0.844 | 0.055 | 80.9 | 161 |
| 18 | 170 | 1500 | 5.0 | 0.021 | 0.907 | 0.032 | 87.7 | 93 |
| 19 | 200 | 500 | 15.0 | 0.182 | 0.823 | 0.060 | 76.4 | 175 |
| 20 | 170 | 1500 | 15.0 | 0.044 | 0.940 | 0.039 | 100 | 114 |
| 21 | 200 | 1500 | 5.0 | 0.10 | 0.90 | 0.02 | 50.0 | 58 |
| 22 | 200 | 1500 | 15.0 | 0.064 | 0.85 | 0.016 | 24.6 | 47 |

Table I shows that when no methyl iodide is employed the production rate of ethylidene diacetate is extremely poor whereas a substantial increase results when one weight percent of methyl iodide is present and that the use of both high temperature and pressure, especially when using greater amounts of methyl iodide, give good to excellent space-time yields but yields of ethylidene diacetate are lower. Table I also shows that ruthenium on carbon, even when used in combination with large amounts of methyl iodide, is a comparatively poor catalyst for hydrogenating acetic anhydride to ethylidene diacetate.

The invention has been described in detail with particular reference to preferred embodiments thereof, but it will be understood that variations and modifications can be effected within the spirit and scope of the invention.

I claim:

1. Process for the preparation of ethylidene diacetate which comprises hydrogenating acetic anhydride at about 140° to 225° C. and about 300 to 2500 psig in the presence of a catalytic amount of ruthenium on alumina and methyl iodide.

2. Process according to claim 1 wherein the amount of metyl iodide is about 1 to 25 weight percent based on the acetic anhydride.

3. Process according to claim 1 for the preparation of ethylidene diacetate which comprises hydrogenating acetic anhydride at about 160° to 180° C. and about 500 to 1000 psig in the presence of a catalytic amount of ruthenium on alumina and about 5 to 10 weight percent of methyl iodide based on the weight of the acetic anhydride.

* * * * *